United States Patent
Nadaoka et al.

(10) Patent No.: US 7,192,784 B2
(45) Date of Patent: Mar. 20, 2007

(54) METHOD OF MEASUREMENT IN CHROMATOGRAPHY

(75) Inventors: Masataka Nadaoka, Iyo (JP); Mie Takahashi, Niihama (JP); Hirotaka Tanaka, Matsuyama (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 210 days.

(21) Appl. No.: 10/019,966

(22) PCT Filed: May 8, 2001

(86) PCT No.: PCT/JP01/03840

§ 371 (c)(1),
(2), (4) Date: May 1, 2002

(87) PCT Pub. No.: WO01/86300

PCT Pub. Date: Nov. 15, 2001

(65) Prior Publication Data

US 2002/0150930 A1    Oct. 17, 2002

(51) Int. Cl.
*G01N 33/53*    (2006.01)
(52) U.S. Cl. ............... 436/518; 435/7.1; 435/4; 435/7.92; 435/7.93; 435/7.94; 435/7.95; 435/288.2; 435/288.6; 435/288.7; 435/507; 435/514; 436/538; 436/541; 436/810
(58) Field of Classification Search ............ 435/4, 435/7.92–7.95, 288.2, 288.6; 436/288.7, 436/507, 514, 518, 538, 541
See application file for complete search history.

(56) References Cited

U.S. PATENT DOCUMENTS

| | | | | | |
|---|---|---|---|---|---|
| 5,206,177 | A | * | 4/1993 | DeLaCroix et al. | 436/518 |
| 5,451,504 | A | * | 9/1995 | Fitzpatrick et al. | 435/7.2 |
| 6,020,209 | A | * | 2/2000 | Narang et al. | 436/514 |
| 6,436,721 | B1 | * | 8/2002 | Kuo et al. | 436/514 |

FOREIGN PATENT DOCUMENTS

| | | | |
|---|---|---|---|
| CA | 2198948 | | 3/1997 |
| EP | 0 291 194 | | 11/1988 |
| EP | 0 724 157 | | 7/1996 |
| EP | 0 895 084 | * | 3/1999 |
| EP | 0 987 551 | | 3/2000 |
| JP | 8-334511 | | 12/1996 |
| JP | 10-274624 | | 10/1998 |
| JP | 10-274653 | | 10/1998 |
| WO | 97/09620 | | 3/1997 |
| WO | 97/35205 | | 9/1997 |

* cited by examiner

*Primary Examiner*—Bao-Thuy L. Nguyen
(74) *Attorney, Agent, or Firm*—Wenderoth, Lind & Ponack, L.L.P.

(57) ABSTRACT

A substantial amount of a marker reagent associated with a measurement is measured in a marker reagent measurement area, and the substantial amount of the marker reagent is reflected by a result obtained in a reaction result measurement area where a reaction with a measurement target in an inspection target solution is measured. Thereby, an influence of external environmental factors, factors in a property of the inspection target solution, an erroneous operation in a measurement operation or the like is eliminated, whereby a chromatography measuring method employing a biosensor with higher accuracy and higher reliability can be provided.

14 Claims, 6 Drawing Sheets

measurement data before correction

Fig.5(b)

measurement data after correction

METHOD OF MEASUREMENT IN CHROMATOGRAPHY

This application is a National Stage of PCT/JP01/03840, filed May 8, 2001.

TECHNICAL FIELD

The present invention relates to a chromatography measuring method and, more particularly, to an improved method for measuring an inspection target solution by a biosensor utilizing chromatography.

BACKGROUND ART

A biosensor, which utilizes a specific reaction produced by an antibody, an enzyme and the like, detects components to be measured in an inspection target solution such as body fluid, thereby enabling application to a clinical field or the like.

As a typical example of qualitatively or quantitatively measuring components to be measured in an inspection target solution (sample) which is detected by such a biosensor, utilizing chromatography, there is an immuno-chromatographic sensor. In this immuno-chromatographic sensor, a development layer for developing the inspection target solution is provided, which includes a reagent part where a reagent is immobilized in a part thereof, and also includes a marker reagent hold part where a marker reagent, which can be eluted by development of the inspection target solution, is held in a dry state. When the a inspection target solution is developed, bonding occurs in the reagent immobilization part and then this bonding amount is measured, whereby components to be measured in the inspection target solution can be measured.

This immuno-chromatographic sensor is generally constituted by an inspection target solution application part where an inspection target solution is applied, and plural development layers, in which an antibody is immobilized in a reagent immobilization part, which is a part of the development layer, and an antibody marked with a marker such as gold colloid particles is held, in a marker reagent hold part which is upstream of the reagent immobilization part in the development layer, in a dry state where it can be eluted by the inspection target solution.

When a required amount of inspection target solution is applied to this immuno-chromatographic sensor, the inspection target solution elutes the marked antibody while permeating porous materials. Then, an amount of the marked antibody, which is the amount of the marked antibody eluted by the inspection target solution being bonded to the antibody in the reagent immobilization part, in the reagent immobilization part is measured, thereby detecting components to be measured in the inspection target solution. Further, the amount of this bonded marked antibody can be measured by visually confirming the amount of the marker, such as gold colloid particles which remains behind as a result of the bonding of the marked antibody in the reagent immobilization part. That is, since the degree of coloration (the depth of a color) in the reagent immobilization part varies with the concentration of an antigen (components to be measured) included in the inspection target solution, the inspector visually checks this, thereby enabling the measurement.

While the description has been given here of a case where a sandwich reaction of an antigen antibody reaction is taken as a measurement principle, the measurement result can also be obtained in a bonding state of the marker reagent in an antibody immobilization part even when other competitive reactions are similarly taken as measurement principles.

Further, while in the above-described example the description is given of a case where the measurement result is visually obtained by a qualitative judgement, Japanese Published Patent Application No. Hei. 8-334511 describes a method by which the degree of coloration in the reagent immobilization part of a specimen is imaged by a CCD to be judged automatically so as to improve a low reproducibility and individual variations of the visual judgement. In a case where a semi-quantitative or more accurate judgement is required as the measurement result, there are a method for reading by a transparent mode employing an optical reading device, which is disclosed in Japanese Published Patent Application No. Hei. 10-274624, and a method for taking-in as an image by a camera or the like to be processed arithmetically, which is disclosed in Japanese Published Patent Application No. Hei. 10-274653.

However, in the above-described conventional methods for measuring a measurement target in an inspection target solution, an elution amount of the marked antibody eluted from the marker reagent hold part by the inspection target solution varies due to factors coming from a dry state of a sensor, a preservation condition of a reagent in the sensor, or an error in reagent concentration in the sensor depending on environments at fabrication of the sensor, factors coming from a property of the inspection target solution, factors coming from an erroneous operation at measurement or environments at the measurement, or the like.

When the elution amount of the marked antibody is constant, the amount of the bonded marked antibody which is obtained by the marked antibody being eluted into the reagent immobilization part and thereby bonded enables more accurate and uniform measurement of the concentration of the measurement target in the inspection target solution. However, when the amount of the eluted marked antibody varies due to the above-described factors, the amount of the marked antibody which is bonded to the reagent immobilization part for each measurement will vary even when the concentration of the measurement target in the inspection target solution is constant.

That is, in a case where the amount of the eluted marked antibody varies due to the factors when the measurement is implemented to obtain a qualitative measurement result, an erroneous measurement result is given especially in the vicinity of a measurement limit high sensitivity.

Further, when the amount of the eluted marked antibody is extremely small, an accurate bonding amount cannot be obtained in the reagent immobilization part.

Moreover, also in the case of implementing a measurement requiring a semi-quantitative or quantitative measurement, the bonding amount of the marked antibody in the reagent immobilization part varies due to variations in the amount of the eluted marked antibody due to the factors, resulting only in a low-accurate measurement. Thus, the above-described methods can only implement at most a qualitative or semi-quantitative measurement at the most and cannot realize a quantitative measurement.

The present invention is made to solve the above-mentioned problems and has for its object to provide a chromatography measuring method which can obtain a more accurate measurement result and enhance its accuracy also of a quantitative measurement.

SUMMARY OF THE INVENTION

According to a first aspect of the present invention, there is provided a chromatography measuring method for measuring components to be measured included in an inspection target solution utilizing chromatography. The method employs a biosensor comprising a development layer where the inspection target solution is developed, a reagent immobilization part formed by immobilizing a reagent in a part of the development layer, and a marker reagent hold part formed by holding a marker reagent in another part of the development layer so as to be eluted by the development of the inspection target solution. A bonding amount of the marker reagent in the reagent immobilization part is measured, thereby determining the quality or quantity of the components to be measured in the inspection target solution, and an amount of eluted marker reagent components or residual marker reagent components which have not been eluted is measured.

Therefore, when a measurement target in the inspection target solution is detected by the bonding amount of the marker reagent in the reagent immobilization part, a substantial amount of the eluted or residual marker reagent which exerts an influence on the bonding amount is measured, thereby allowing appropriateness of the bonding amount of the marker reagent components (reliability of bonding amount data) at the immobilization part to be known, resulting in an enhancement in the accuracy of a measurement operation. Further, by measuring the elution amount or the residual amount, a correction according to the elution amount is performed for the bonding amount of the marker reagent components in the reagent immobilization part, thereby reflecting an amount of the marker reagent components associated with actual measurement, resulting in a more accurate chromatography measuring method employing a biosensor.

According to a second aspect of the present invention, in the chromatography measuring method as defined in accordance with the first aspect, the bonding amount of the marker reagent in the reagent immobilization part is corrected by employing the amount of the eluted marker reagent components or residual marker reagent components which have not been eluted.

Therefore, it is possible to reflect the amount of the marker reagent components associated with the actual measurement, resulting in a more accurate chromatography measuring method employing a biosensor.

According to a third aspect of the present invention, in the chromatography measuring method as defined in accordance with the first or second aspects, the measurement of the amount of the eluted marker reagent components or residual marker reagent components which have not been eluted employs an optical detector.

Therefore, it is possible to numerically express the amount of the eluted marker reagent components more accurately, resulting in a more accurate chromatography measuring method employing a biosensor.

According to a fourth aspect of the present invention, in the chromatography measuring method as defined in accordance with any of the first to third aspects, the measurement of the amount of the eluted marker reagent components is performed in a part other than the reagent immobilization part.

Therefore, the amount of the eluted marker reagent components is measured in a part other than the reagent immobilization part, which is unaffected by the amount of the measurement target components, whereby a more accurate amount of the eluted marker reagent can be measured, thereby realizing a more accurate chromatography measuring method employing a biosensor.

According to a fifth aspect of the present invention, in the chromatography measuring method as defined in accordance with any of the first to fourth aspects, the measurement of the amount of the eluted marker reagent components is performed before the bonding amount of the marker reagent is measured in the reagent immobilization part.

Therefore, the amount of the marker reagent associated with the bonding produced in the reagent immobilization part can be previously known, thereby enhancing the accuracy of the measurement operation as well as enabling a more rapid judgement, resulting in a more accurate chromatography measuring method employing a biosensor.

BRIEF DESCRIPTION OF DRAWINGS

FIGS. 2(a)–2(c) are diagrams illustrating states after an inspection target solution is applied in the immuno-chromatographic sensor according to the first embodiment of the invention; wherein

FIGS. 3(a) and 3(b) are perspective views exemplifying an order of areas to be measured by a biosensor in a chromatography measuring method according to the first embodiment of the invention; wherein

FIGS. 6(a) and 6(b) are perspective views exemplifying another order of areas to be measured by the biosensor in the chromatography measuring method according to the first embodiment of the invention; wherein

DETAILED DESCRIPTION OF THE PREFERRED EMBODIMENTS

Embodiment 1

Hereinafter, a first embodiment of to the present invention will be described with reference to FIGS. 1 to 6(b).

Figure 1:
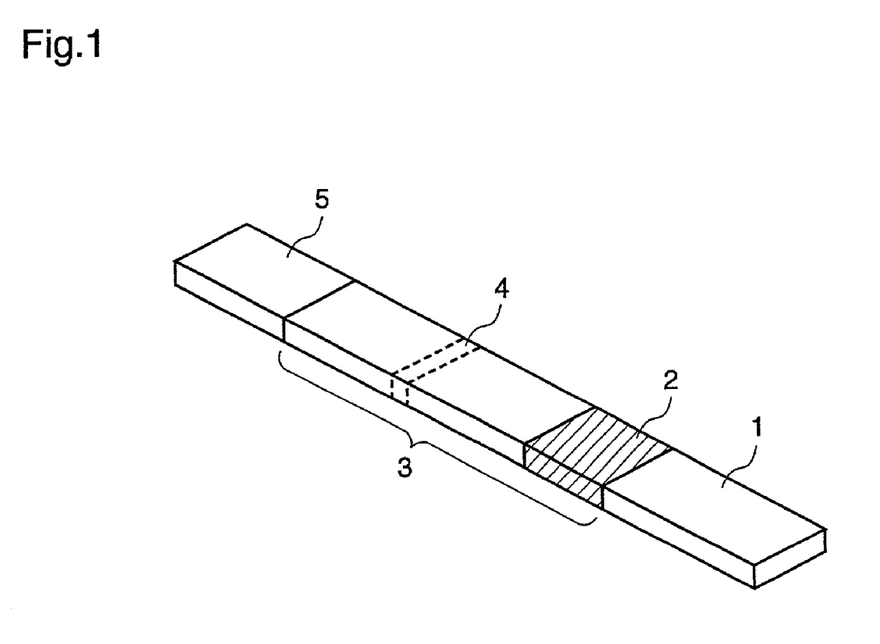
FIG. 1 is a perspective view illustrating structure of an immuno-chromatographic sensor according to a first embodiment of the present invention.

FIG. 1 is a diagram illustrating structure of an immuno-chromatographic sensor that is used when a chromatography measuring method according to the first embodiment of the present invention is implemented.

In FIG. 1, the immuno-chromatographic sensor according to the first embodiment comprises an inspection target solution application part 1 where an inspection target solution is applied, an antibody immobilization film 3 (development layer) which includes a marker reagent hold part 2 and an antibody immobilization part 4 (reagent immobilization part), and a water absorbing part 5.

The inspection target solution application part 1 is a part to which an inspection target solution is applied and which is made of a nonwoven fabric as a material that can be penetrated by the inspection target solution. In addition to the nonwoven fabric, any arbitrary materials which can be penetrated by the inspection target solution, such as glass fiber filter paper and a membrane filter, can be employed as a material used for this inspection target solution application part 1.

Further, the marker reagent hold part 2 is a part that holds a marker reagent in a part of the antibody immobilization film 3. This marker reagent is an antibody marked with a gold colloid as a marker, which is held in a dry state so as to be eluted by permeation of the inspection target solution. While, in the first embodiment, an antibody marked with a gold colloid is used as the marker reagent, it is possible to select an enzyme, a protein, coloring matters, a fluorescence, a metallic sol, a nonmetallic sol, and coloring particles such as a latex, in addition to the gold colloid, as the marker. Further, an antigen, a hapten, a protein or the like, in addition to the antibody, is available as a reagent to be marked with the marker.

Further, the antibody immobilization part 4 is a part that fixes and holds an antibody in a dry state in a part of the antibody immobilization film 3 other than the marker reagent hold part 2. This antibody is not eluted in the inspection target solution but has a property of being bonded to the marker reagent in the marker reagent hold part 2 which is eluted in the inspection target solution. Thus, the antibody in the antibody immobilization part 4 can be bonded to and capture the marker reagent in the antibody immobilization part 4.

In the immuno-chromatographic sensor according to the first embodiment, a sandwich reaction is employed; that is, an antibody is provided in the marker reagent hold part 2 and a measurement target in the inspection target solution is an antigen. However, when a competitive reaction is employed, an antigen is taken as the measurement target in the inspection target solution and the antigen is provided in the marker reagent hold part 2, and further when an antigen antibody reaction is employed, various patterns depending on user's selection are also available.

The antibody immobilization film 3, which includes the marker reagent hold part 2 and the antibody immobilization part 4, is composed of cellulose nitrate. A material employed for this antibody immobilization film 3 may be any material which can be penetrated by the inspection target solution, in addition to the cellulose nitrate.

Further, the water absorbing part 5 absorbs the inspection target solution which passes through the antibody immobilization film 3, and is composed of glass fiber filter paper. In addition to the glass fiber filter paper, any arbitrary material which can be penetrated by the inspection target solution, such as a nonwoven fabric and a resin porous material, are available as a material of this water absorbing part 5.

According to the first embodiment, the inspection target solution is dropped onto this so-constituted immuno-chromatographic sensor and developed on the antibody immobilization film 3, and an elution amount of the marker reagent eluted from the marker reagent hold part 2 or the residual amount on the marker reagent hold part 2 after the elution is detected, whereby the accuracy of a measurement operation is enhanced. Further, a correction corresponding to the amount of the eluted marker reagent is added to a bonding amount of the marker reagent in the antibody immobilization part 4, whereby the amount of the marker reagent associated with actual measurement can be reflected, thereby realizing a chromatography measuring method by which a measurement target, which is included in the inspection target solution, can be measured more accurately.

Hereinafter, a description will be given of the chromatography measuring method by which the measurement target that is included in the inspection target solution is detected by the immuno-chromatographic sensor according to the first embodiment.

Figures 2A, 2B, 2C:
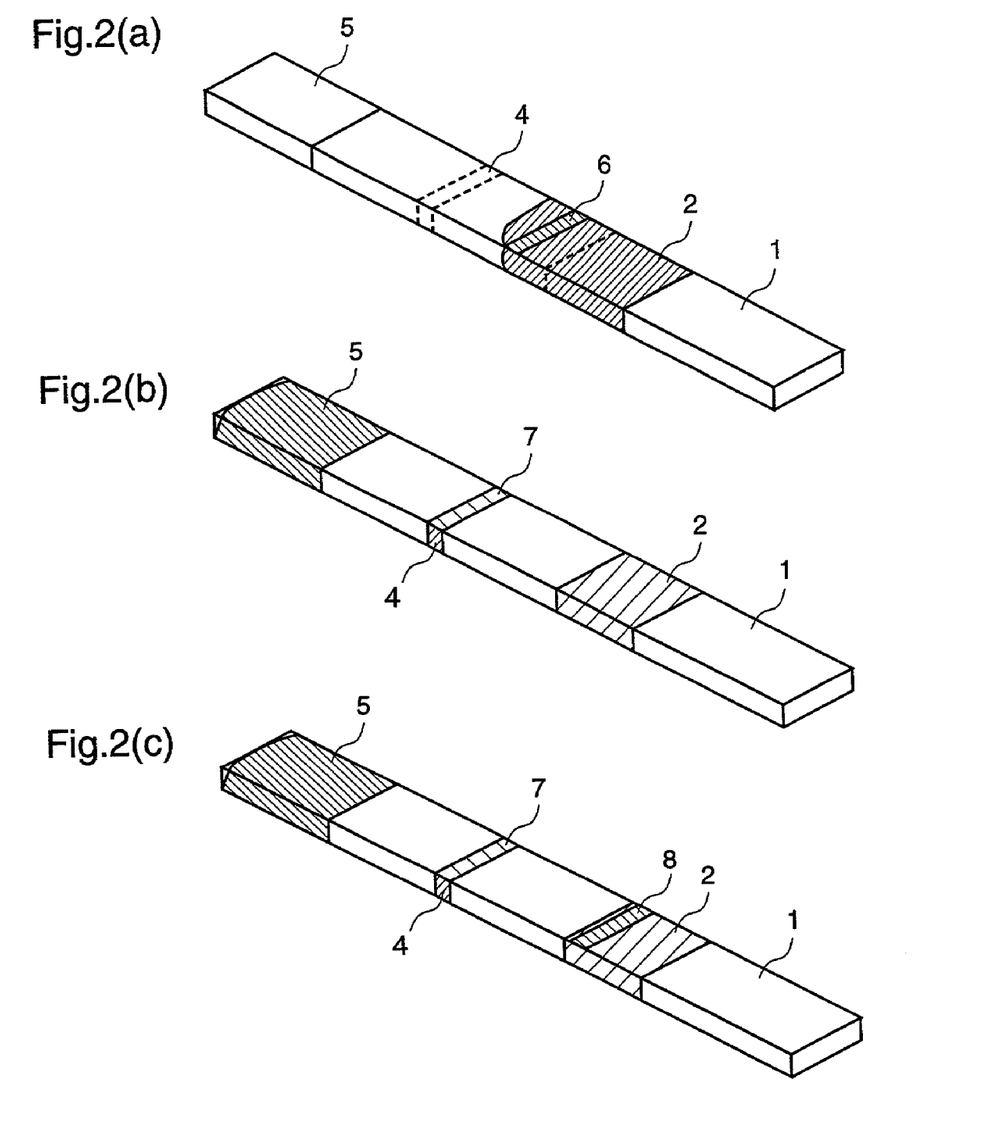
FIG. 2(a) illustrates an initial state after the inspection target solution is applied.
FIGS. 2(b) and 2(c) illustrate states at measurement of a bonding amount of a marker reagent.

FIGS. 2(*a*)–2(*c*) illustrate states of the immuno-chromatographic sensor after the inspection target solution is applied to the inspection target solution application part 1.

FIG. 2(*a*) illustrates a state of the immuno-chromatographic sensor at a time when a relatively shorter time has elapsed since the inspection target solution is applied to the inspection target solution application part 1. In this figure, numeral 6 denotes an area where the amount of the eluted marker reagent is measured. In FIG. 2(*a*), the inspection target solution which is applied to the inspection target solution application part 1 starts permeation into the water absorbing part 5 while eluting the marker reagent in the marker reagent hold part 2. At this point in time, the marker reagent eluted by the inspection target solution does not reach the antibody immobilization part 4.

FIG. 2(*b*) illustrates a state of the immuno-chromatographic sensor at a time of measurement of a bonding amount of the marker reagent in the antibody immobilization part 4. In this figure, numeral 7 denotes an area where the bonding amount of the marker reagent is measured in the antibody immobilization part 4. In FIG. 2(*b*), the inspection target solution which has passed through the antibody immobilization film 3 is absorbed in the water absorbing part 5, and a reaction corresponding to the amount of the measurement target in the inspection target solution is seen in the antibody immobilization part 4.

FIG. 2(*c*) illustrates a state of the immuno-chromatographic sensor at the same point in time as shown in FIG. 2(*b*). In this figure, numeral 8 denotes an area where the residual amount of the marker reagent is measured.

As described above, the measurement of the amount of eluted marker reagent components is performed in an area other than the antibody immobilization part 4. This is because the bonding amount of the marker reagent varies with the amount of the measurement target in the inspection target solution in the antibody immobilization part 4, whereby when the marker reagent is to be read a specified time after the measurement is started, it cannot be judged whether or not its value results from the bonding reaction of the measurement target.

Further, the amount of the eluted marker reagent is measured before the measurement of the bonding amount of the marker reagent in the antibody immobilization part 4 (upstream of the antibody immobilization part 4). This is because after the inspection target solution is applied in the measurement operation, the inspection target solution develops on the antibody immobilization film 3 while it passes through the marker reagent hold part 2 before passing through the antibody immobilization part 4 and the marker reagent components is eluted, whereby when the amount of the eluted marker reagent is previously measured before the marker reagent passes through the antibody immobilization part 4 as a measurement part, it can promptly reflect measurement of the amount of the marker reagent bonded in the antibody immobilization part 4.

Further, when there is no inconvenience even if such prompt correction is not performed, it is also possible that the amount of the marker reagent is measured in the marker reagent bonding amount measurement area 7 on the antibody immobilization part 4, and thereafter a corresponding measurement value reflects a measurement value obtained in the remaining marker reagent amount measurement area 8 in the state shown in FIG. 2(c).

Hereinafter, the chromatography measuring method according to the first embodiment will be described in more detail with reference to FIGS. 1 to 6, taking quantity determination of hCG (human chorionin gonadotropin) in urine as a specific example of the chromatography measuring method employing a biosensor according to the first embodiment. Here, the measurement method of the first embodiment is not restricted to the quantity determination of hCG.

First, as a specimen (immuno-chromatographic sensor) according to the first embodiment, there is manufactured an immuno-chromatographic specimen which includes an anti-hCG-β antibody immobilization line and a broad band of a complex of an anti-hCG-α antibody and a gold colloid in a nitrocellulose film.

As shown in FIG. 1, the specimen comprises the antibody immobilization film 3 made of a nitrocellulose film, which includes the antibody immobilization part 4 where the anti-hCG-β antibody is immobilized and the marker reagent hold part 2 including the complex of the anti-hCG-α antibody and gold colloid before (upstream of) the antibody immobilization part 4, the inspection target solution application part 1 made of a nonwoven fabric, and the water absorbing part 5 made of a glass fiber.

Figures 3A, 3B:
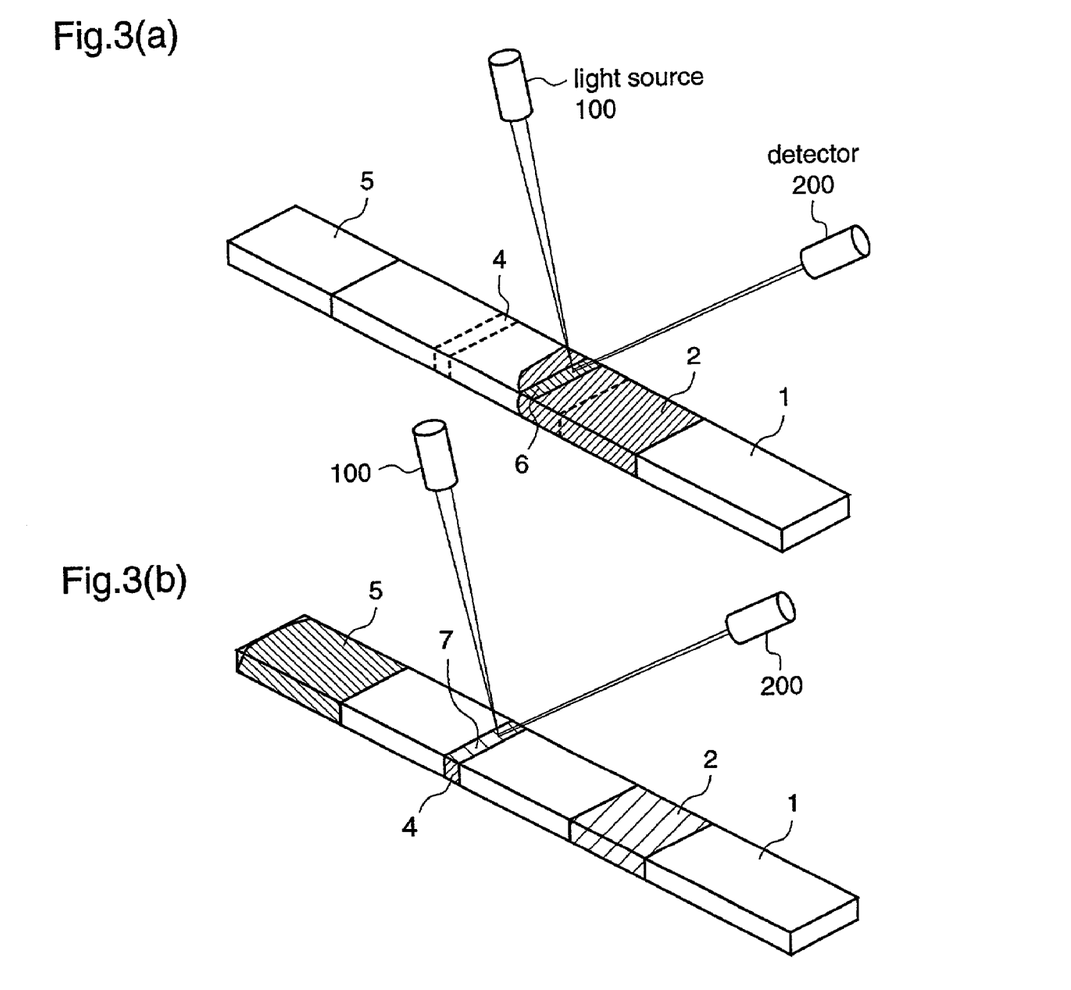
FIG. 3(a) is a diagram illustrating an area to be measured first.
FIG. 3(b) is a diagram illustrating an area to be measured next.

The first embodiment uses a following correction method: a hCG solution is applied to the specimen shown in FIG. 1, a reflection absorbance in eluted marker reagent amount measurement area 6 is measured by a reflective spectrophotometer (CS9300; Shimadzu Corporation) as shown in FIG. 3(a), by irradiating the eluted marker reagent amount measurement area 6 with an inspection light from a light source 100 and receiving its reflected light by a detector 200. Then, as shown in FIG. 3(b), a reflection absorbance in marker reagent bonding amount measurement area 7 is measured by the reflective spectrophotometer in the same way as in FIG. 3(a) and further the reflection absorbance in the marker reagent bonding amount measurement area 7 is corrected by employing reflection absorbance in the eluted marker reagent amount measurement area 6.

Hereinafter, a description will be given of A: a method for creating the specimen, B: a method for preparing the inspection target solution, and C: examination of the correction method.

A. Creation of the Chromatographic Specimen

The anti-hCG-β antibody solution which was diluted with a phosphate buffer solution to control concentration was prepared. This antibody solution was applied on the nitrocellulose film by employing a solution discharge device. Thereby, a detecting antibody immobilization line (antibody immobilization part 4) was obtained on the nitrocellulose film. After being dried, this nitrocellulose film was immersed in a Tris-HCl buffer solution including 1% skim milk, and gently shaken for thirty minutes. Thirty minutes later, the film was moved into a Tris-HCl buffer solution tank, gently shaken for ten minutes, and thereafter gently shaken in another Tris-HCl buffer solution tank for another ten minutes, thereby washing the film. After being washed twice, the film was removed from cleaning fluid and dried at room temperatures.

The gold colloid was prepared by adding 1% citric acid solution to a refluxing 100° C.-solution of 0.01% chloroauric acid. After the reflux was continued for thirty minutes, it was cooled. The anti-hCG-α antibody was added to a gold colloid solution which was prepared to pH9 by using a 0.2M potassium carbonate solution, then this obtained solution was stirred for several minutes, and thereafter a 10% BSA (bovine serum albumin) solution pH9 was added thereto by such an amount that a 1% solution was finally obtained, and stirred. Thereby, an antibody-gold colloid complex (marker antibody) was prepared. The 2 marker antibody solution was centrifuged at 4° C. and 20000 G for fifty minutes, whereby the marker antibody was isolated, and this isolated marker antibody was suspended in a cleaning buffer solution (1% BSA•phosphate buffer solution) and thereafter centrifuged to wash and isolate the marker antibody. After being suspended in the cleaning buffer solution and filtrated through a 0.8 cm filter, the marker antibody was prepared to be one-tenth as much as the initial gold colloid solution and stored at 4° C.

The marker antibody solution was set in the solution discharge device and applied to a position where an anti-hCG-β antibody is apart from the immobilization dry film on the antibody immobilization position, and thereafter the film was dried. Thereby, the marker antibody hold part (marker reagent hold part) 2 was obtained on the antibody immobilization film 3.

The antibody immobilization film 3 including the antibody immobilization line 4 and the marker antibody hold part 2 prepared as described above was affixed on a reactive layer carrier support (not shown), a nonwoven fabric was added thereto as the inspection target solution application part 1, glass fiber filter paper was added thereto as the water absorbing part 5, and thereafter the film was cut into small pieces of 0.5 cm width, thereby manufacturing the specimen.

B. Preparation of the Inspection Target Solution

The hCG solution of a known concentration is added into human urine, thereby preparing hCG solutions of various known concentrations.

C. Examination of the Correction Method

Hereinafter, a description will be given of the correction method using a reflection absorbance assuming that the measurement of the marker reagent bonding amount is performed five minutes later and the measurement of the eluted marker reagent amount is performed one minute later and three minutes later.

To perform correction, it is required to previously obtain coefficients inherent to the device (specimen). First, to obtain coefficients of the manufactured device, urine having a 1000 IU/1 hCG concentration is prepared, and more than 200 µl of the urine is applied onto the inspection target solution application part 1 of the specimen (the number of specimens N=10). With the application of the inspection target solution as a start time, a reflection absorbance in the eluted marker reagent amount measurement area 6 is measured one minute and three minutes after the measurement start is measured employing the reflective spectrophotometer (CS9300; manufactured by Shimadzu Corporation). Then, five minutes later, a coloration state in the marker reagent bonding amount measurement area 7 is measured employing the reflective spectrophotometer as described above. Taking the reflection absorbance in the eluted marker reagent amount measurement area 6 one minute later as an absorbance $A_T$, the reflection absorbance three minutes later as an absorbance $B_T$, and the measurement result in the marker reagent bonding amount measurement area 7 as an absorbance CT, its measurement result is plotted and the following relational expression (1) is derived. This measurement result is shown in FIG. 4(*b*).

$$Y=1.12X+D \text{ (provided that } X=A_T+B_T\text{)} \quad (1)$$

Figure 4A:
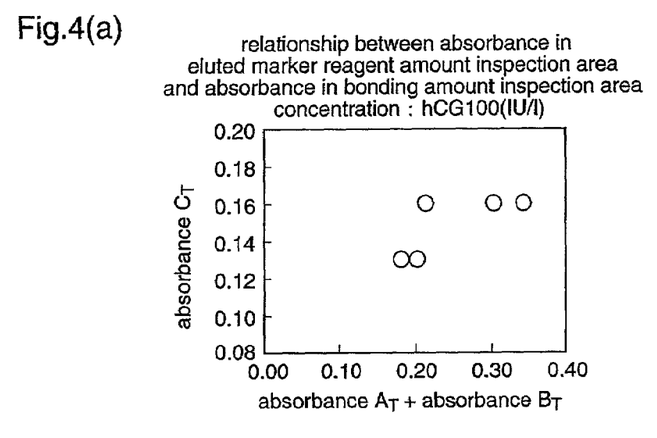
FIGS. 4(a)–4(c) are diagrams illustrating a relationship between absorbances $A_T+B_T$ and an absorbance $C_T$ at each concentration of hCG measured by a biosensor according to the first embodiment of the invention.
Figure 4B:
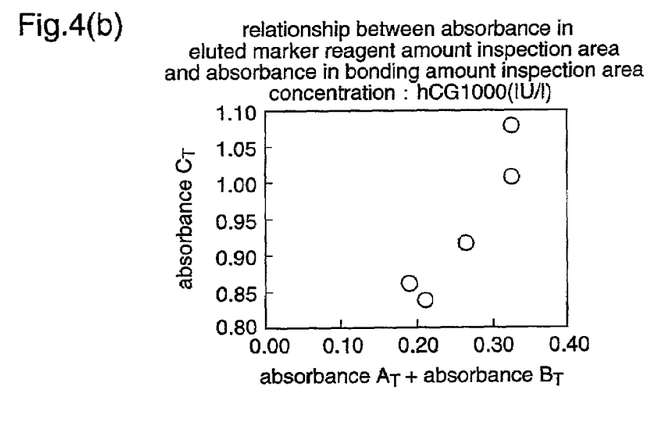
Figure 4C:
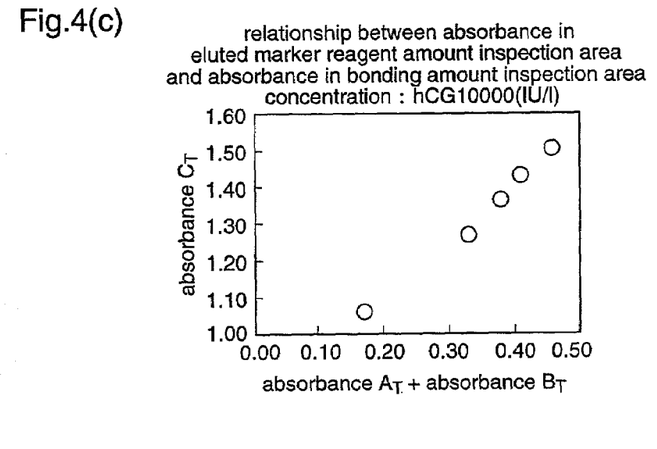

Here, Y denotes the absorbance in the marker reagent bonding amount measurement area 7, which is represented by the ordinate in FIGS. 4(*a*)–4(*c*). Further, X denotes the sum of the absorbances in the eluted marker reagent amount measurement area 6, which is represented by the abscissas in FIGS. 4(*a*)–4(*c*). D denotes a constant.

Next, a central value of the measurement results in the eluted marker reagent amount measurement area 6 is obtained. The central value of all measurements is 0.29 in the first embodiment.

Thus, coefficients inherent to the device (biosensor), i.e., E=1.12 and F=0.29, are obtained. The coefficient E inherent to the device is the slope of the relational expression of the absorbances in the eluted marker reagent amount measurement area 6 and the marker reagent bonding amount measurement area 7, and the coefficient F is the central value of the absorbances obtained in the eluted marker reagent amount measurement area 6.

Next, the hCG solution of a known concentration is added into human urine, whereby urine including hCG of 100, 1000, 10000 IU/l is prepared, a measurement is performed by the chromatography measuring method according to the first embodiment employing the inspection target solution of the three kinds of known concentrations, and a measurement value before correction is compared with a measurement value after the correction.

First, more than 200 μl of urine including the above-described hCG concentration is applied to the inspection target solution application part 1 on the specimen for urine of each hCG concentration and is developed toward the water absorbing part 5, thereby starting the measurement. With the application of the inspection target solution as a start time, the reflection absorbance in the eluted marker reagent amount measurement area 6 one minute and three minutes after the start was measured employing the reflective spectrophotometer (CS9300; manufactured by Shimadzu Corporation). Thereafter, the coloration state in the marker reagent bonding amount measurement area 7 five minutes later was measured employing the reflective spectrophotometer in the same manner as described above. Assume that the reflection absorbance one minute later in the eluted marker reagent amount measurement area 6 is an absorbance $A_T$, the reflection absorbance three minutes later is an absorbance $B_T$, and the measurement result five minutes later in the marker reagent bonding amount measurement area 7 is an absorbance $C_T$.

FIGS. 4(*a*)–4(*c*) are diagrams showing the relationship between the sum of the absorbance $A_T$ and absorbance $B_T$ and the absorbance $C_T$ at each concentration of hCG which is the measurement target in the inspection target solution. FIGS. 4(*a*), 4(*b*) and 4(*c*) illustrate the relationship between the sum of the absorbance $A_T$ and absorbance $B_T$ and the absorbance $C_T$ when the hCG concentration is 100 IU/l, 1000 IU/l and 1000 IU/l, respectively. From FIGS. 4(*a*) to 4(*c*), it can be seen that the sum of the absorbance $A_T$ and absorbance $B_T$ correlates with the absorbance $C_T$ at each hCG concentration.

Next, using the above-described measurement result and the coefficients of the device, the correction of the absorbance $C_T$ for the measurement result of the marker reagent bonding amount measurement area 7 is performed employing the following expression (2), thereby obtaining a correction value $C_H$.

$$\text{Correction value } C_H = C_T \times (1-((A_T+B_T)-F \times E)) \quad (2)$$

Here, $C_H$ denotes a corrected result.

Figure 5A:
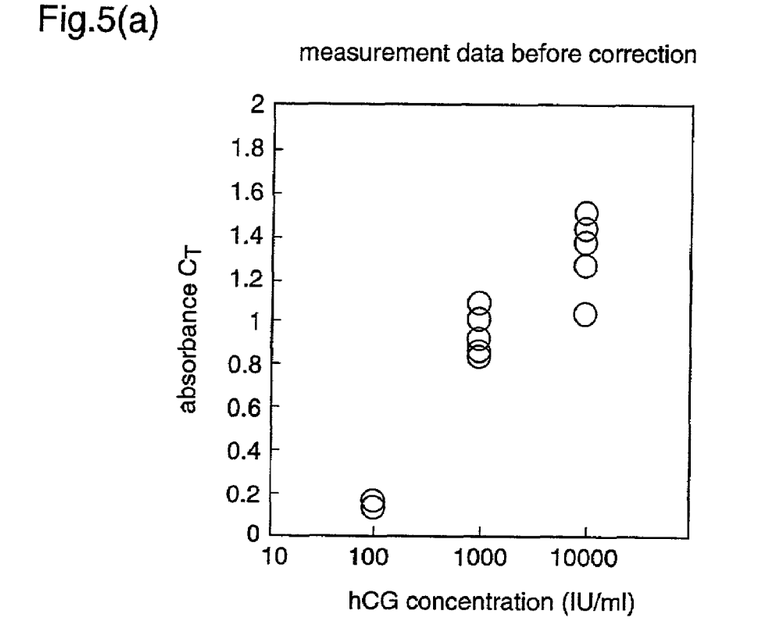
FIGS. 5(a) and 5(b) are diagrams illustrating a measurement result before correction (FIG. 5(a)) and a measurement result after the correction (FIG. 5(b)) at each hCG concentration measured by the biosensor according to the first embodiment of the invention.
Figure 5B:
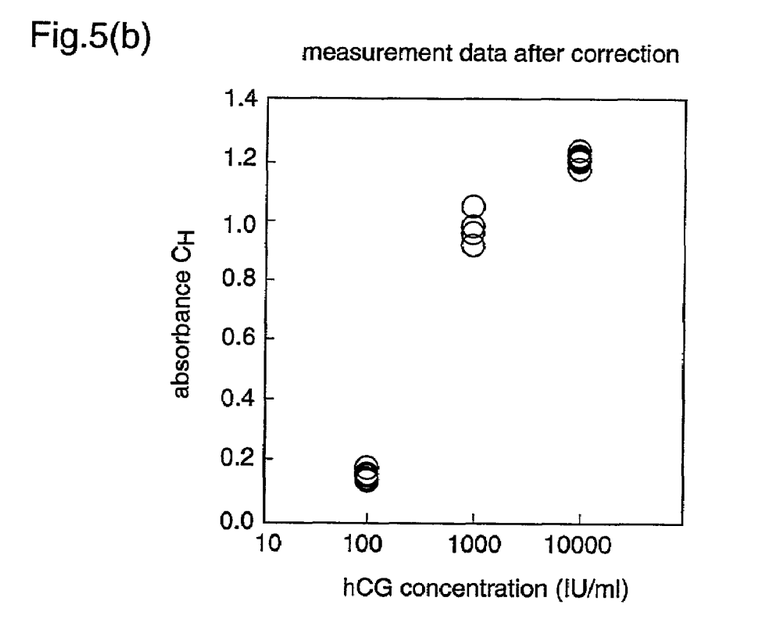
Figures 6A, 6B:
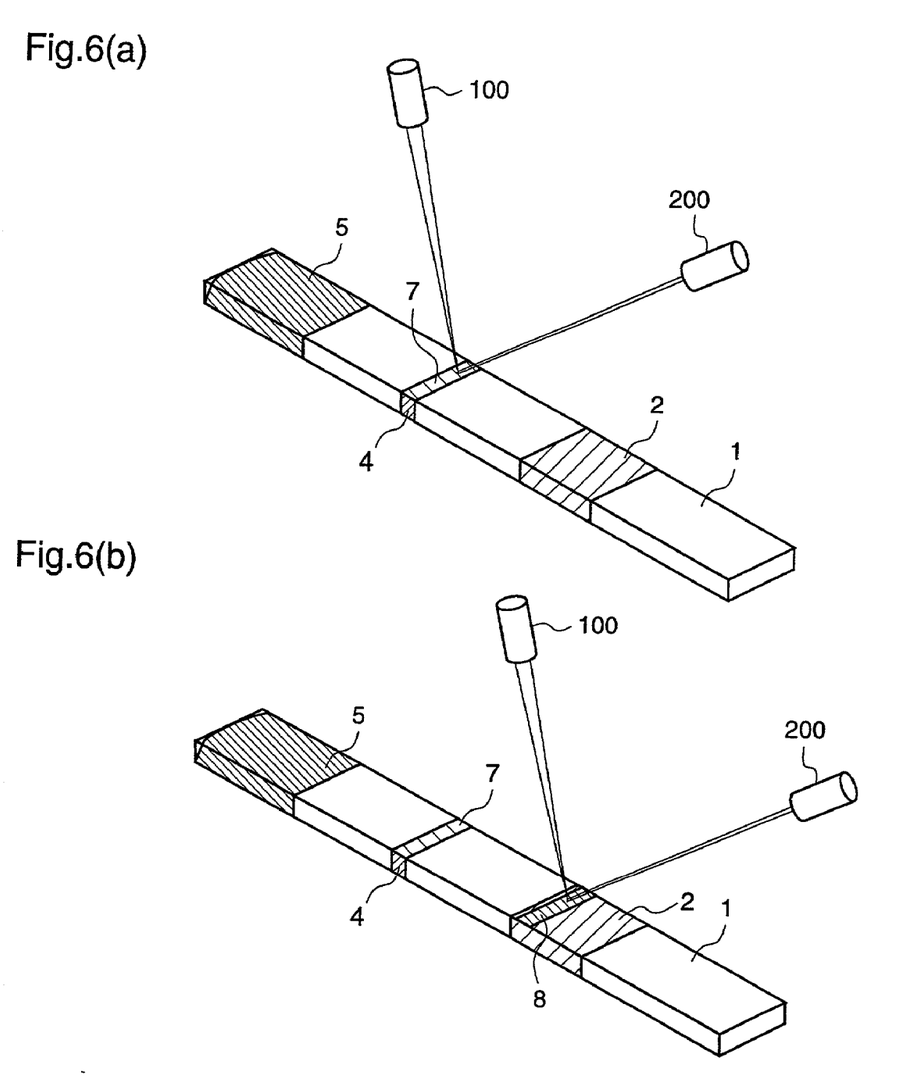
FIG. 6(a) is a diagram illustrating an area to be measured first.
FIG. 6(b) is a diagram illustrating an area to be measured next.

FIGS. 5(*a*) and 5(*b*) are diagrams illustrating measurement data before the correction and measurement data after the correction in the marker reagent bonding amount measurement area 7 is measured at each hCG concentration. FIG. 5(*a*) is a diagram showing the results in FIGS. 4(*a*)–4(*c*), which are before the correction, being re-plotted for each hCG concentration, and FIG. 5(*b*) is a diagram showing measurement results after the correction, which is performed employing the expression (2) for the measurement results shown in FIGS. 4(*a*)–4(*c*), being re-plotted for each hCG concentration.

CV values (variation coefficient) of the same hCG concentration before the correction, which are 11.1%, 10.8% and 13.8%, respectively, become 8.9%, 4.1%, and 1.9%, respectively, because of the correction, whereby it can be seen that the accuracy of measurement values is greatly enhanced in all concentration areas. Accordingly, by implementing the correction, the accuracy of a measurement value is dramatically enhanced, and even if the amount of the eluted marker reagent components varies, the measurement value is hardly influenced by the variations when the hCG concentration is the same, thereby greatly enhancing the accuracy of quantitative determination.

In the above descriptions, a case where the amount of the eluted marker reagent is measured to perform the correction has been explained in detail. However, in a case where the residual amount of the marker reagent is measured to perform the correction, the reflection absorbance in the marker reagent bonding amount measurement area 7 is obtained first by the same reflective spectrophotometer as that in FIGS. 3(*a*) and 3(*b*) (see FIG. 6(*a*)), the reflection absorbance in the marker reagent residual amount measurement area 8 is obtained next (see FIG. 6(*b*)), the reflection absorbance in the marker reagent bonding amount measurement area 7 is corrected by the reflection absorbance in the marker reagent residual amount measurement area 8, thereafter a value inherent to the device is calculated in the same way as in the measurement of the amount of the eluted marker reagent as described above, and the correction is performed by the expression (2) employing the calculated value.

As described above, according to the chromatography measuring method in the first embodiment, even when the amount of the eluted marker reagent components varies due to factors in the sensor part, such as a dry state of the sensor, a preservation condition of reagent components in the sensor, and external conditions such as temperature, humidity, and a manufacturing time at sensor manufacture, factors in a property of the inspection target solution, or factors at the measurement operation, such as an erroneous operation in the measurement operation and environments at the measurement operation, the elution amount or residual amount of the marker reagent is detected, thereby enhancing accuracy of the measurement operation. Further, by measuring the elution amount or the residual amount, a correction corresponding to the elution amount is performed for the bonding amount of the marker reagent components in the reagent immobilization part, thereby providing a more accurate chromatography measuring method.

While, in the first embodiment, description has been given of a correction method by which the specimen as shown in FIG. 1 is employed, a shape of the specimen is not restricted to that shown in FIG. 1 and can be selected properly.

Further, values E and F inherent to the device vary due to factors such as a marker reagent holding concentration, a marker reagent holding area, a marker reagent holding amount, a kind of the reagent marker, fluid rate, a kind of sample solvent and positions of the marker reagent holding area and an immobilized reagent, and values can be properly selected as required.

In addition, a method for measuring an elution amount, a position of an area where the elution amount is measured, correcting arithmetic expressions or the like can be properly selected as required.

APPLICABILITY IN INDUSTRY

A chromatography measuring method according to the present invention is useful as a method by which a more accurate measurement result is achieved when a bonding amount of a marker reagent in a reagent immobilization part is measured to determine quality or quantity of components to be measured in an inspection target solution.

The invention claimed is:

1. A chromatography measuring method comprising:
   providing a biosensor having
   (i) a development portion,
   (ii) a label reagent held in a first part of said development portion in a dry state, said label reagent being elutable by a test sample comprising an analyte, and
   (iii) an immobilized reagent in a second part of said development portion,
   wherein said label reagent in said first part binds to said analyte in said test sample, and said immobilized reagent in said second part is a reagent that specifically binds to a complex comprising said analyte and the labeled reagent;
   developing said test sample on said development portion;
   using an optical detector to measure in an area between said first and second parts of said development portion that does not include said second part of said development portion, an amount of said label reagent eluted from said first part of said development portion;
   using an optical detector to measure, in said second part of said development portion, an amount of any label reagent bound to said immobilized reagent in said second part of said development portion;
   correcting the measured amount of said label reagent bound to said immobilized reagent in said second part of said development portion, on the basis of a relationship between the measured amount of said label reagent eluted from the first part of said development portion and a total amount of said label reagent present in said first part of said development portion before application of said test sample; and
   calculating a concentration of said analyte in said test sample on the basis of the corrected amount of said label reagent bound to said immobilized reagent in said second part of said development portion.

2. The chromatography measuring method according to claim 1, wherein
   using an optical detector to measure the amount of said label reagent eluted from said first part of said development portion is performed prior to using an optical detector to measure the amount of said label reagent bound to said immobilized reagent in said second part of said development portion.

3. The chromatography measuring method according to claim 1, wherein
   using an optical detector to measure the amount of said label reagent eluted from said first part of said development portion comprises measuring said amount of said label reagent, eluted from said first part of said development portion, before said test sample passes said second part of said development portion.

4. The chromatography measuring method according to claim 1, wherein
   using an optical detector to measure the amount of said label reagent eluted from said first part of said development portion comprises measuring said amount of said label reagent, eluted from said first part of said development portion, before said label reagent binds to any immobilized reagent.

5. A chromatography measuring method comprising:
   providing a biosensor having
   (i) a development portion,
   (ii) a label reagent held in a first part of said development portion in a dry state, part of said label reagent being elutable by a test sample comprising an analyte, and
   (iii) an immobilized reagent in a second part of said development portion,
   wherein said label reagent in said first part binds to said analyte in said test sample, and said immobilized reagent is a reagent that specifically binds to a complex comprising said analyte and the labeled reagent;
   developing said test sample on said development portion;
   using an optical detector to measure, in said second part of said development portion, an amount of said label reagent so as to obtain an amount of said label reagent bound to said immobilized reagent in said second part of said development portion;
   using an optical detector to measure, in a measurement area of said first part of said development portion, an amount of residual label reagent not eluted from said first part of said development portion by the developing of said test sample;
   correcting the obtained amount of said label reagent bound to said immobilized reagent in said second part of said development portion, on the basis of a relationship between the measured amount of residual label reagent not eluted from said first part of said development portion and a total amount of said label reagent present in said first part of said development portion before application of said test sample; and
   calculating a concentration of said analyte in said test sample on the basis of the corrected amount of said label reagent bound to said immobilized reagent in said second part of said development portion.

6. The chromatography measuring method according to claim 5, wherein
   using an optical detector to measure the amount of residual label reagent not eluted from said first part of said development portion is performed prior to using an optical detector to measure the amount of said label reagent so as to obtain the amount of said label reagent bound to said immobilized reagent in said second part of said development portion.

7. The chromatography measuring method according to claim 5, wherein
   using an optical detector to measure the amount of residual label reagent not eluted from said first part of said development portion comprises measuring said amount of said residual label reagent, not eluted from said first part of said development portion, before said label reagent, eluted from said first part, becomes bonded to any immobilized reagent.

8. A chromatography measuring method comprising:
providing a biosensor having
  (i) a development portion,
  (ii) a label reagent held in a first part of said development portion in a dry state, said label reagent being elutable by a test sample comprising an analyte, and
  (iii) an immobilized reagent in a second part of said development portion,
  wherein said label reagent in said first part binds to and reacts with said immobilized reagent while said label reagent is in said inspection target solution after having been eluted by said test sample, and said immobilized reagent in said second part is a reagent with which said label reagent and analyte competitively bind;
developing said test sample on said development portion;
using an optical detector to measure, in a measurement area between said first and second parts of said development portion that does not include said second part of said development portion, an amount of said label reagent eluted from said first part of said development portion;
using an optical detector to measure, in said second part of said development portion, an amount of said label reagent bound to said immobilized reagent in said second part of said development portion;
correcting the measured amount of said label reagent bound to said immobilized reagent in said second part of said development portion, on the basis of a relationship between the measured amount of said label reagent eluted from said first part of said development portion and a total amount of said label reagent present in said first part of said development portion before application of said test sample; and
calculating a concentration of said analyte in said test sample on the basis of the corrected amount of said label reagent bound to said immobilized reagent in said second part of said development portion.

9. The chromatography measuring method according to claim 8, wherein
using an optical detector to measure the amount of said label reagent eluted from said first part of said development portion is performed prior to using an optical detector to measure the amount of said label reagent bound to said immobilized reagent in said second part of said development portion.

10. The chromatography measuring method according to claim 8, wherein
using an optical detector to measure the amount of said label reagent eluted from said first part of said development portion comprises measuring said amount of said label reagent, eluted from said first part of said development portion, before said test sample passes said second part of said development portion.

11. The chromatography measuring method according to claim 8, wherein
using an optical detector to measure the amount of said label reagent eluted from said first part of said development portion comprises measuring said amount of said label reagent, eluted from said first part of said development portion, before said label reagent binds to any immobilized reagent.

12. A chromatography measuring method comprising:
providing a biosensor having:
  (i) a development portion,
  (ii) a label reagent held in a first part of said development portion in a dry state, part of said label reagent being elutable by a test sample comprising an analyte, and
  (iii) an immobilized reagent in a second part of said development portion,
  wherein said label reagent in said first part binds to and reacts with said immobilized reagent while said label reagent is in said test sample after having been eluted by said test sample, and said immobilized reagent is a reagent with which said label reagent and analyte competitively bind;
developing said test sample said development portion;
using an optical detector to measure, in said second part of said development portion, an amount of said label reagent so as to obtain an amount of said label reagent bound to said immobilized reagent in said second part of said development portion;
using an optical detector to measure, in a measurement area of said first part of said development portion, an amount of residual label reagent not eluted from said first part of said development portion;
correcting the obtained amount of said label reagent bound to said immobilized reagent in said second part of said development portion, on the basis of a relationship between the measured amount of residual label reagent not eluted from said first part of said development portion and a total amount of said label reagent present in said first part of said development portion before application of said test sample; and
calculating a concentration of said analyte in said test sample on the basis of the corrected amount of said label reagent bound to said immobilized reagent in said second part of said development portion.

13. The chromatography measuring method according to claim 12, wherein
using an optical detector to measure the amount of residual label reagent not eluted from said first part of said development portion is performed prior to using an optical detector to measure the amount of said label reagent so as to obtain the amount of said label reagent bound to said immobilized reagent in said second part of said development portion.

14. The chromatography measuring method according to claim 12, wherein
using an optical detector to measure the amount of residual label reagent not eluted from said first part of said development portion comprises measuring said amount of said residual label reagent, not eluted from said first part of said development portion, before said label reagent, eluted from said first part becomes bonded to any immobilized reagent.

* * * * *

UNITED STATES PATENT AND TRADEMARK OFFICE
CERTIFICATE OF CORRECTION

| | |
|---|---|
| PATENT NO. | : 7,192,784 B2 |
| APPLICATION NO. | : 10/019966 |
| DATED | : March 20, 2007 |
| INVENTOR(S) | : Masataka Nadaoka et al. |

It is certified that error appears in the above-identified patent and that said Letters Patent is hereby corrected as shown below:

ON THE TITLE PAGE

1. Please insert item 30 --Foreign Application Priority Data, May 8, 2000 (JP).......2000-134342--.

2. Item 57, line 1, "with a" should read --with--.

Signed and Sealed this

Thirtieth Day of October, 2007

JON W. DUDAS
*Director of the United States Patent and Trademark Office*